United States Patent [19]

Carr et al.

[11] Patent Number: 5,792,137
[45] Date of Patent: Aug. 11, 1998

[54] COAGULATING MICROSYSTEM

[75] Inventors: William N. Carr, Bloomfield; Lewis T. Ladocsi, Short Hills, both of N.J.

[73] Assignee: Lacar Microsystems, Inc., Livingston, N.J.

[21] Appl. No.: 549,541

[22] Filed: Oct. 27, 1995

[51] Int. Cl.[6] .................................................. A61B 17/38
[52] U.S. Cl. ........................... 606/29; 606/31; 606/32; 606/40; 606/52
[58] Field of Search ................................. 606/27–30, 32

[56] References Cited

U.S. PATENT DOCUMENTS

| | | | |
|---|---|---|---|
| 702,472 | 6/1902 | Pignolet | 606/29 |
| 1,497,975 | 6/1924 | Flick et al. | 606/28 |
| 2,310,844 | 2/1943 | Draeger | 606/29 |
| 3,117,578 | 1/1964 | Helbling | 606/28 |
| 3,768,482 | 10/1973 | Shaw | 606/29 |
| 4,449,528 | 5/1984 | Auth et al. | 606/31 |
| 5,100,355 | 3/1992 | Marcus et al. | |
| 5,201,992 | 4/1993 | Marcus et al. | |
| 5,204,581 | 4/1993 | Andreadakis et al. | |
| 5,266,530 | 11/1993 | Bagley et al. | |

OTHER PUBLICATIONS

Appl. Phys. Lett. 56(3), 15 Jan. 1990—R. B. Marcus et al.—'Formation of silicon tips with <nm radius'—(pp. 236–238).
J. Vac. Sci. Technol. B 9(6), Nov./Dec. 1991—T.S. Ravi et al.—'Oxidation sharpening of silicon tips'—(pp. 2733–2737).
J. Electrochem. Soc., vol. 139, No. 6, Jun. 1992—J. M. Kim et al. 'Control in Microengineering'—(pp. 1700–1705).

*Primary Examiner*—David M. Shay
*Attorney, Agent, or Firm*—Ohlandt, Greeley, Ruggiero & Perle

[57] ABSTRACT

A coagulating microknife includes at least one knife blade that is comprised of a doped semiconductor body that exhibits a resistive current-carrying characteristic and a sharp cutting edge. A power supply is connected to the knife blade and applies a metered current which heats the knife blade to a controlled temperature for cauterizing tissue during a cutting action. The semiconductor body includes a pair of contact areas which extend into the body and enable localized heating at the tip of the knife blade.

7 Claims, 6 Drawing Sheets

COAGULATING MICROSYSTEM

FIELD OF THE INVENTION

This invention relates to an apparatus for concurrently cutting/cauterizing tissue and, more particularly, to such an apparatus which employs a semiconductor material as the cutting/cauterizing instrumentality.

BACKGROUND OF THE INVENTION

Presently, devices used for cauterizing tissue also cause collateral damage to surrounding tissue areas. If cautery is required near vital anatomical structures, great care must be taken to control the amount of heat applied to the tissue. This problem is especially severe in the field of microsurgery where small vessels are cauterized after being cut during a surgical procedure. Notwithstanding the potential for collateral tissue damage, cauterization is widely used to control fluid and blood loss during surgery. Cauterization also enables a surgeon to avoid the need to suture cut vessels, cauterization seals the blood vessel without the need for suturing—and thereby enabling the surgical procedure to be accomplished more rapidly.

Disposable, cutting instruments and cautery heads are known in the prior art, but are characteristically expensive. In the present-day environment of cost consciousness, any disposable instrument and/or device must exhibit a low cost or else it will not be accepted by the medical community. Thus, low cost disposable devices must, of necessity, be processed so that economies of scale and concurrent processing can be achieved. In the field of semiconductor-based devices, the cost benefits of batch processing enable achievement of extremely inexpensive—but highly complex—semiconductor chip-based devices.

Recently, the field of semiconductor microengineering has shown an ability to produce micro-size devices by use of silicon processing techniques that are widely available in the semiconductor industry. For example, scanning electron microscopes use cold cathode electron emitters to enable imaging of microsurfaces. Such emitters have been constructed from silicon substrates and have been configured in the form of cones having extraordinarily sharp points (exhibiting point radii as little as one nanometer or less). Such structures are produced by an etch process which leaves a tapered, highly-sharpened silicon tip extending from the silicon substrate. In addition to taking the form of a cone, such sharpened silicon structures have also taken the form of needles, pyramids, wedges and ridges.

Details regarding the method of manufacture of such field emission structures can be found in the following articles and patents: "Reactive Ion Etching Techniques for Silicon Sidewall Angle Control in Micro-engineering" Kim et al, *Journal of the Electrochemical Society*, Volume 139, No. 6, Jun. 19, 1992, pages 1700–1705; "Oxidation Sharpening of Silicon Tips" Ravi, et al, *Journal of Vacuum Science Technology*, B9(6), November/December 1991, pages 2733–2737; "Formation of Silicon Tips with Less Than 1 nm Radius" Marcus, et al, *Applied Physics Letters*, Volume 56, No. 3, January 1990, pages 236–238; and in U.S. Pat. No. 5,100,355 to Marcus et al; U.S. Pat. No. 5,201,992 to Marcus et al; U.S. Pat. No. 5,204,581 to Andreadakis et al; and U.S. Pat. No. 5,266,530 to Bagley et al.

There is a need for a replaceable/disposable instrument which enables concurrent cutting and cautery of tissue, while reducing heat damage to surrounding tissue.

Accordingly, it is an object of this invention to provide an improved coagulating microknife for surgical uses.

It is another object of this invention to provide an improved coagulating microknife wherein the operative portion thereof is disposable.

It is another object of this invention to provide an improved coagulating microknife system wherein an amount of heat applied to the tissue is precisely metered, thereby reducing collateral tissue damage.

SUMMARY OF THE INVENTION

A coagulating microknife includes at least one knife blade that is comprised of a doped semiconductor body that exhibits a resistive current-carrying characteristic and a sharp cutting edge. A power supply is connected to the knife blade and applies a metered current which heats the knife blade to a controlled temperature for cauterizing tissue during a cutting action. The semiconductor body includes a pair of contact areas which extend into the body and enable localized heating at the tip of the knife blade.

DETAILED DESCRIPTION OF THE INVENTION

Figure 1:
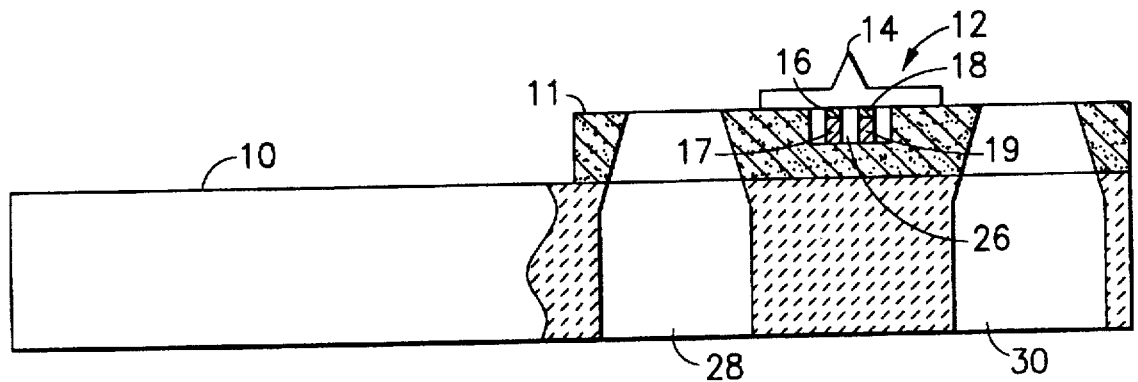
FIG. 1 is a side sectional view of a knife blade and carrier, constructed in accordance with the invention.
Figure 2:
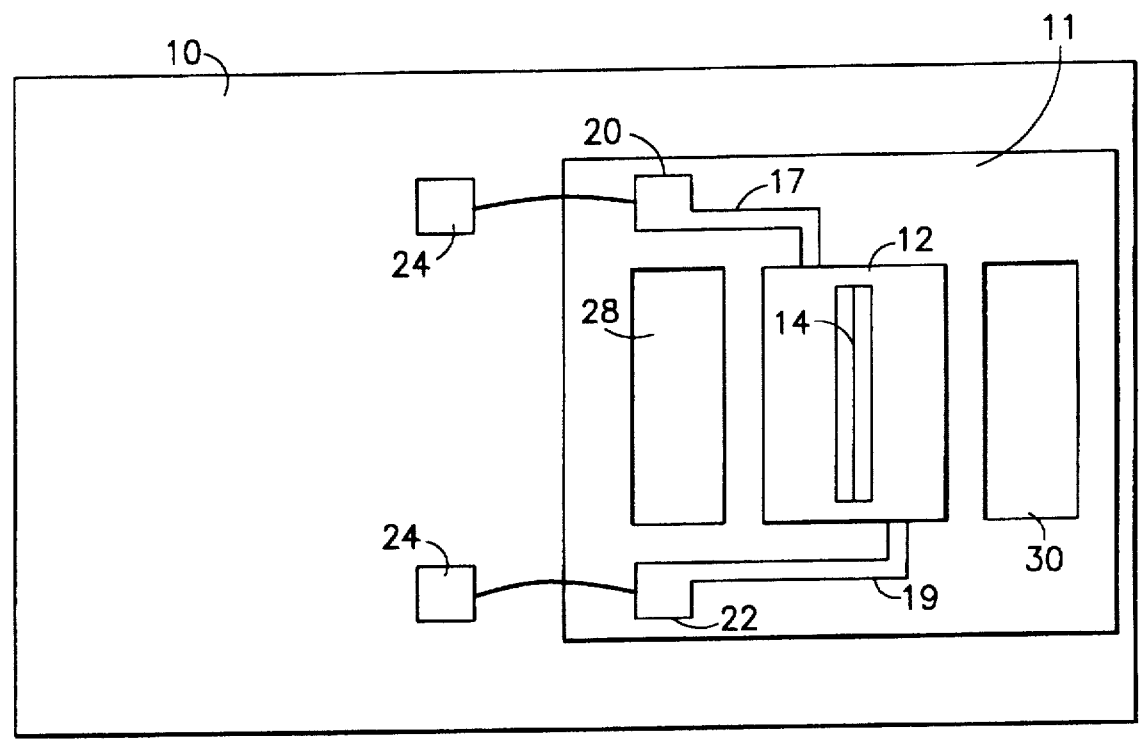
FIG. 2 is a plan view of the knife blade and carrier of FIG. 1.

In FIGS. 1 and 2, the structure (magnified) of a coagulating microknife is illustrated. A ceramic, semiconductor or other compatible substrate 10 is configured to be insertable into the distal end of the pair of forceps. A silicon support wafer 11 is mounted on substrate 10 and supports a cutter wafer 12 (preferably comprised of silicon) that is bonded thereto. Cutter wafer 12 includes an upwardly extending blade 14. A pair of electrical contacts 16 and 18 connect to the lowermost surface of cutter wafer 12 and enable application of an electrical current thereto. A mating pair of electrodes 17 and 19 are mounted on support wafer 11 and connect to contacts 16 and 18, respectively, thereby enabling application of a voltage thereacross. A channel 26 enables electrodes 17 and 19 to access and connect to contacts 16 and 18. A pair of apertures 28 and 30 extend entirely through support wafer 11 and substrate 10 to enable a viewing of a vessel being cut/cauterized by blade 14.

As shown in FIG. 2, conductors 17 and 19 extend out onto the uppermost surface of support wafer 11 and include a pair of bond pads 20 and 22. Wire bond connections can be made between bond pads 20 and 22 to further pads 24 on substrate 10 for further interconnection to a pulsed power supply (to be described below).

Figure 3:
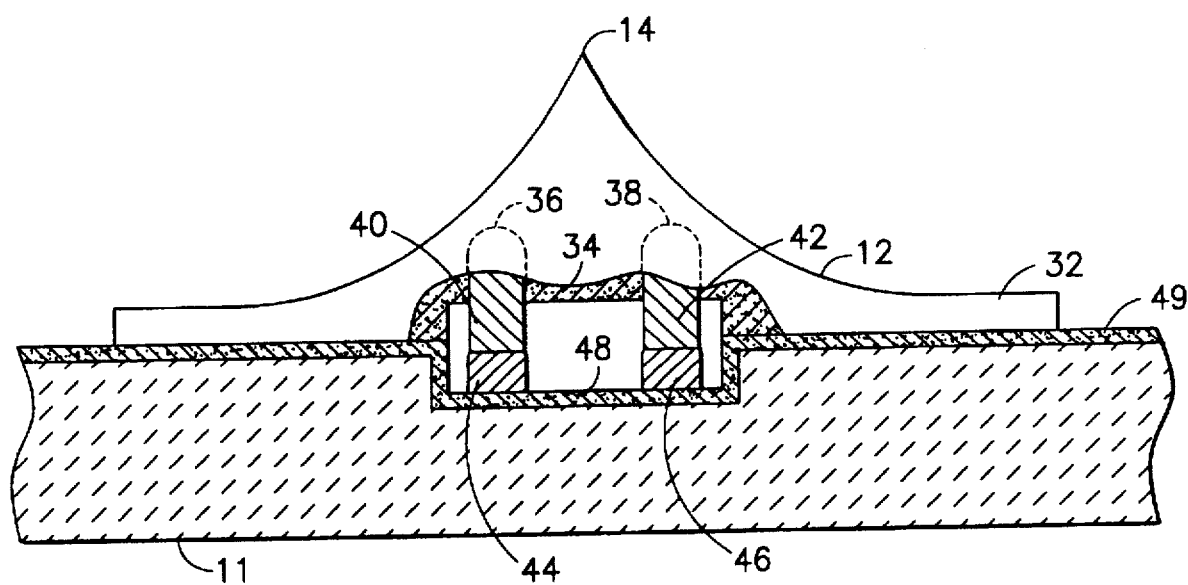
FIG. 3 is an enlarged sectional view of the knife blade of FIG. 1.

In FIG. 3, further details are shown of support wafer 11 and cutter wafer 12. To produce the structure shown in FIG. 3, cutter wafer 12 has a boron etch-stop layer 32 implanted into its lowermost surface. A lithographic mask is positioned on the uppermost surface of cutter wafer 12 (before it takes the shape shown in FIG. 3). The mask comprises an island extending along the length of the surface area that is to become blade 14. An isotropic etch procedure is then performed on the uppermost surface of cutter wafer 12 using, for instance, a mixture of nitric, hydrofluoric and acetic acids, to enable creation of blade shape 14. Reactive ion etching or ion milling processes can also be used to provide a similar cutting tip configuration. To further sharpen blade 14, an oxidation layer is provided on blade 14, followed by a stripping action to remove the oxide and further isotropic etching.

Before blade 14 is produced, a channel 34 is etched into the lowermost surface of cutter wafer 12, a mask applied and a dopant implanted therethrough to create a pair of enhanced conduction contact regions 36 and 38. Thereafter, a pair of metal conductors 40 and 42 are deposited thereon to enable application of power thereto. A mating pair of conductors 44 and 46 reside in a channel 48 in support wafer 11. A silicon dioxide or silicon nitride layer 49 insulates conductors 44 and 46 from each other and from the semiconductor material comprising support wafer 11.

After support wafer 11 and cutter wafer 12 have been configured as shown in FIG. 3, they are joined by a heating process which further enables fusion of conductor combinations 40, 44 and 42, 46, respectively. External extensions of conductors 44 and 46 on support wafer 11 make contact with connector pads that enable connections to be made to a power supply.

Cutter wafer 12 is preferably comprised of silicon which is doped to exhibit a high resistivity. When a voltage is supplied between contact regions 36 and 38, a current flows causing a resistive heating within the region directly beneath blade 14. Through appropriate control of the applied power, blade 14 (and adjoining portions of cutter wafer 12) can be brought to a high temperature to enable cauterization of tissue being concurrently cut by blade edge 14. Electrical connection from regions 36 and 38 is made via inter-wafer connections 40,44 and 42,46 to bonding pads 24 and a connected pulsed power supply.

Figure 4:
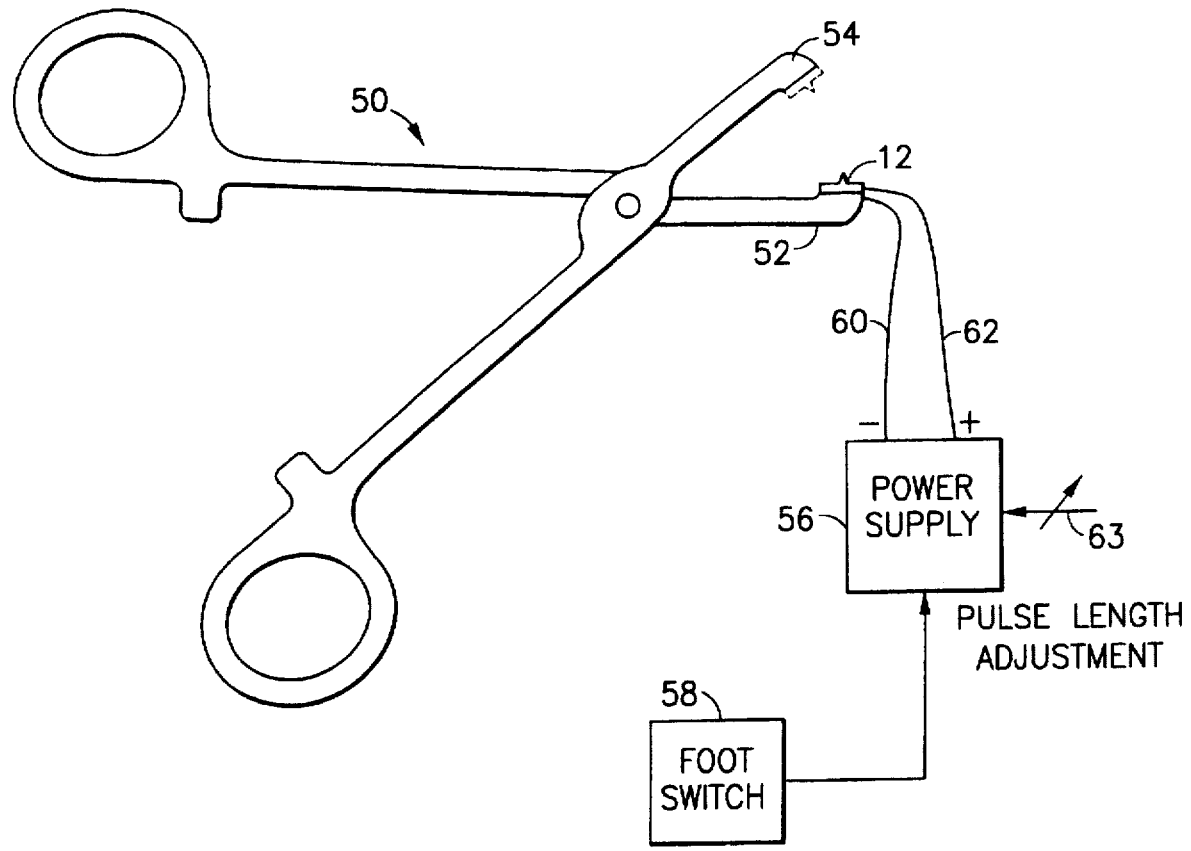
FIG. 4 is a schematic illustrating the mounting of a knife blade constructed in accordance with the invention on a pair of forceps.

In FIG. 4, a pair of forceps 50 are illustrated having a pair of grip jaws 52 and 54. A cutter/cauterizing structure such as shown in FIG. 3 is mounted on grip jaw 52 and is, in turn, connected to a power supply 56. A foot switch 58 controls power supply 56 to apply a voltage to lines 60 and 62. Both the magnitude of the voltage applied to lines 60 and 62 and the length of time of application of the voltage are controlled by the user-adjustable input 63. Thus, the amount of power supplied to cutter wafer 12 by conductors 60, 62 can be precisely controlled so as to achieve a known temperature therein.

More specifically, the amount of applied power is increased if larger vessels are being cut and cauterized and less power is required in the case of smaller vessels. In either instance, a voltage magnitude/pulse length adjustment of power supply 56 assures a precise quantum of power applied to cutter wafer 12 and a concomitant level of heat applied to the tissue being cut.

Figure 5:
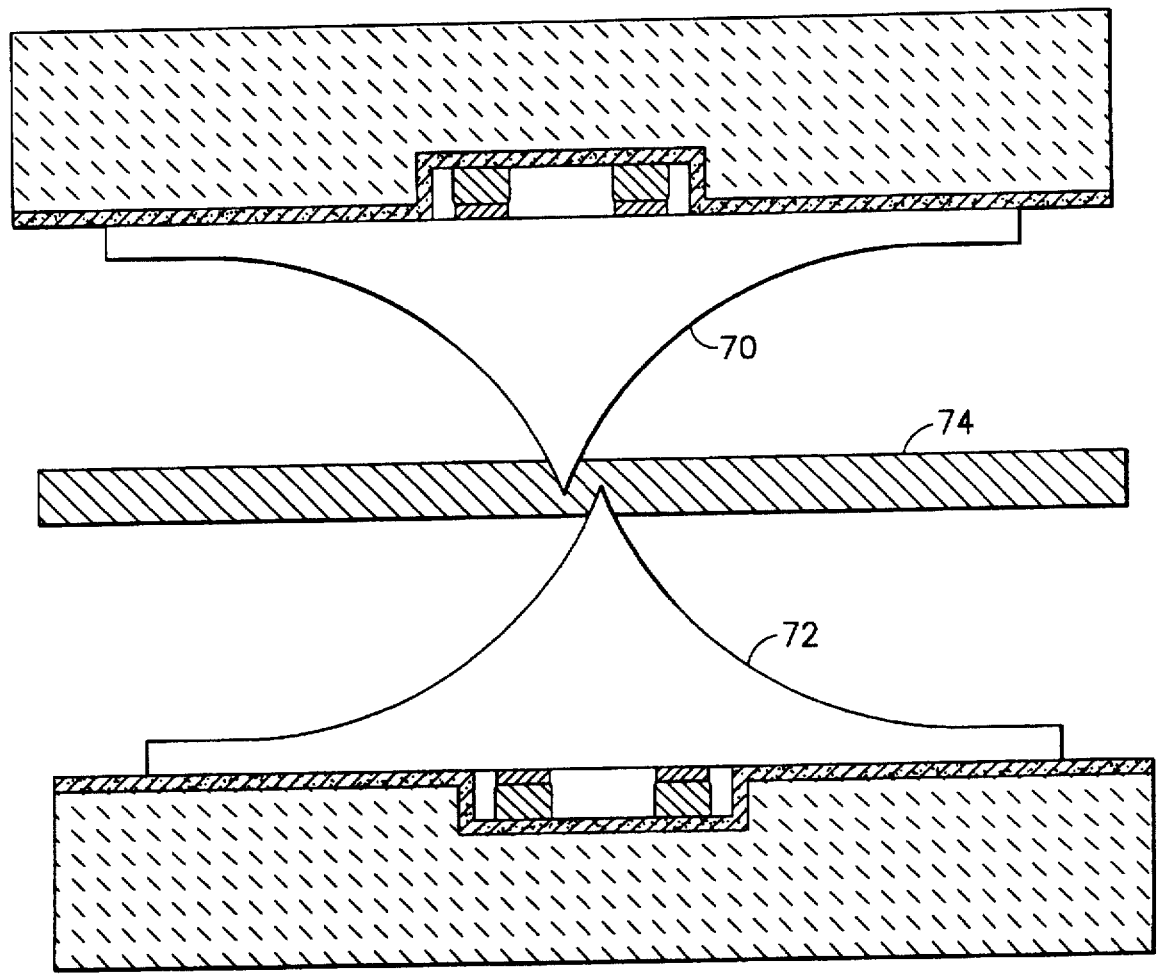
FIG. 5 illustrates a pair of opposed knife blades that are constructed in accordance with the invention.

As will become apparent, a further cutter wafer can be applied to grip end 54 for a shearing type cut action. Such a structure is shown in FIG. 5 wherein a pair of cutter wafers 70 and 72, when brought together, create a scissors-like action on a vessel 74. Each of cutter wafers 70 and 72 is identical in structure to that described in FIG. 3 and is, further, connected to power supply 56 so that each can provide a cauterizing action to vessel 74.

Figure 6:
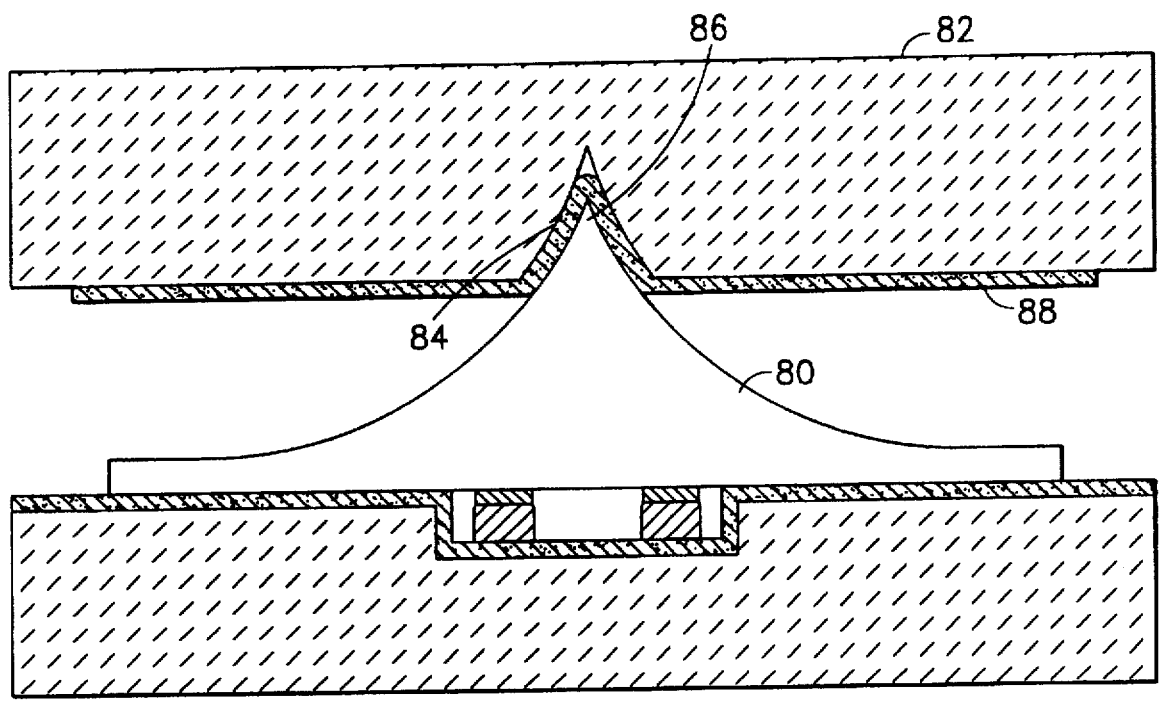
FIG. 6 illustrates still another embodiment of the invention.

In FIG. 6, a further cutting configuration is shown wherein a cutter wafer 80 mates with an anvil structure 82 which includes a wedge-shaped slot 84 for receiving blade 86. When a vessel 88 is positioned between blade 86 and slot 84, not only does a single cut occur, but both ends of vessel 88 are cauterized at the same time by being forced against blade 86 by the walls of slot 84.

Figure 7:
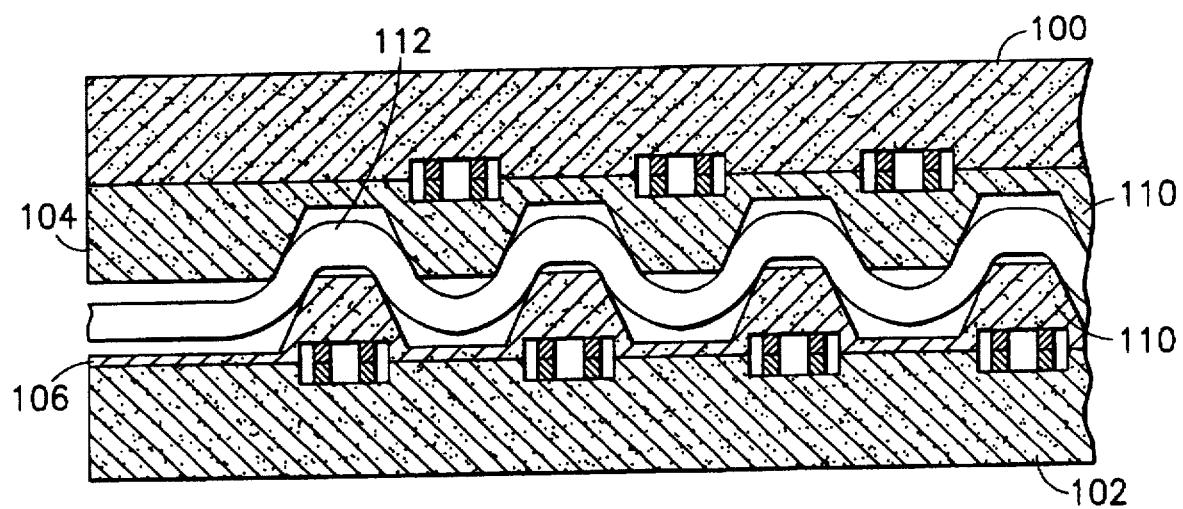
FIG. 7 illustrates a further embodiment of the invention employed for cautery.

In FIG. 7, a sectional view of a cautery version of the invention is illustrated. Support wafers 100 and 102 provide substrates for a pair of opposed cautery wafers 104 and 106 which each include a plurality of truncated pyramids 110. Each pyramid 110 is heated in the manner aforedescribed, and is positioned to mate with a corresponding depression on the opposed substrate. Thus, when a vessel 112 is positioned therebetween, support wafers brought together as shown in the Figure, and pyramids 110 heated, a cautery action is achieved. Further, while FIG. 7 shows a single row of pyramids 110, those skilled in the art will realize that the cautery structure can be configured as a two-dimensional array of rows and columns of pyramids 110 to achieve a wide area cautery action.

The truncated pyramid shapes shown in FIG. 7 are readily obtained in silicon wafers oriented in the [100] crystallographic plane by using a potassium hydroxide as a wet etchant. The sidewalls of the pyramidal shapes are [111] crystallographic planes.

The embodiments described above can be mass produced using micromachining techniques to create precise replicas of specific knife/pyramid shapes, types and dimensions. A single 5-inch diameter wafer can be processed to create approximately 1,000 microknife/cautery heads. This mass production equates to a low cost per device.

The method of producing the cutting edge in each cutting wafer is well known in the prior art and is compatible with most standard silicon semiconductor processing techniques. The microknife can further be heated to extremely high temperatures, as necessary. This contrasts to existing cauterizing blades that are metal, experience breakage of heating elements due to thermal coefficient of expansion mismatch and cannot be heated to high heats as a result of potential damage to the temper of the metal.

The ability to precisely control the amount of power applied to a cutter/cautery wafer enables the surgeon to produce a cauterizing action which inflicts minimal damage on collateral tissue. Further, the adjustability of the applied power enables a matching of the level of heat dissipation to the diameter of the blood vessel being cut/cauterized.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A coagulating microknife comprising:
   at least one doped silicon semiconductor body, micromachined to a knife blade form and exhibiting a resistive current carrying characteristic and a sharp cutting edge; and
   power supply means connected to said silicon semiconductor body for applying a metered current thereto, to heat said knife blade form to a controlled temperature for cauterizing tissue during a cutting action by said knife blade form of said tissue.

2. The coagulating microknife as recited in claim 1, further comprising:

an insulating substrate for supporting said silicon semiconductor body in a cutting configuration and including at least one aperture to enable a user to view the tissue being cut.

3. The coagulating microknife as recited in claim 1, further comprising:

an insulating substrate for supporting said silicon semiconductor body in a cutting configuration said insulating substrate configured to removably mate with a receiving structure at a distal end of a pair of forceps.

4. The coagulating microknife as recited in claim 1, wherein said power supply means includes a user-operable switch for enabling application of said metered current to said silicon semiconductor body, and adjustment means for enabling control of an amount of power applied to said silicon semiconductor body.

5. The coagulating microknife as recited in claim 1, wherein said silicon semiconductor body includes a pair of spaced apart conductive contact regions for distributing current flow across an interior area of said knife blade form.

6. The coagulating microknife as recited in claim 1, further comprising:

a second doped silicon semiconductor body micromachined to have a knife blade form and movably mounted in opposition to said at least one doped silicon semiconductor body, and exhibiting a resistive current carrying characteristic and a sharp cutting edge;

means for connecting said second doped silicon semiconductor body to said power supply means so as to enable current flow therethrough concurrently with current flow through said at least one doped silicon semiconductor body; and means for bringing together in a shearing action, said at least one knife blade form and said second knife blade form.

7. The coagulating microknife as recited in claim 1, further comprising:

a substrate mounted in opposition to said at least one knife blade form and including a channel for receiving a cutting edge of said at least one knife blade form; and means for bringing together in a cutting action, said at least one knife blade form and said substrate.

* * * * *